(12) United States Patent
Hamilton et al.

(10) Patent No.: US 6,468,477 B1
(45) Date of Patent: Oct. 22, 2002

(54) SEALABLE AIR SAMPLING BAG

(75) Inventors: Steven D. Hamilton, Greenfield; Lyle H. Hamilton, Brookfield, both of WI (US)

(73) Assignee: Hamilton Enterprises, Milwaukee, WI (US)

( * ) Notice: Subject to any disclaimer, the term of this patent is extended or adjusted under 35 U.S.C. 154(b) by 0 days.

(21) Appl. No.: 09/497,972

(22) Filed: Feb. 4, 2000

(51) Int. Cl.[7] .............................. A61B 5/08; B65D 81/00
(52) U.S. Cl. ........................ 422/84; 422/102; 600/532; 600/543
(58) Field of Search ................................ 422/102, 119, 422/84, 85; 383/52, 109, 111, 202; 229/103.1; 137/223; 446/224; 428/42.1; 600/532, 543

(56) References Cited

U.S. PATENT DOCUMENTS

| | | |
|---|---|---|
| 3,303,840 A | 2/1967 | Etzlinger |
| 3,410,300 A * | 11/1968 | Mondano .................... 383/52 |
| 3,817,108 A | 6/1974 | Principe et al. |
| 3,923,043 A | 12/1975 | Yanda |
| 4,327,741 A | 5/1982 | Watson |
| 4,544,273 A | 10/1985 | Berndt |
| 4,585,254 A * | 4/1986 | Adams ......................... 283/81 |
| 4,671,298 A | 6/1987 | Babb et al. |
| 4,852,583 A | 8/1989 | Walker |
| 4,947,861 A | 8/1990 | Hamilton |
| 5,042,500 A | 8/1991 | Norlien et al. |
| 5,042,501 A | 8/1991 | Kenny et al. |
| 5,066,597 A * | 11/1991 | Stinson et al. .............. 435/311 |
| 5,100,005 A * | 3/1992 | Noble et al. ................. 209/583 |
| 5,140,993 A | 8/1992 | Opekun, Jr. et al. |
| 5,165,393 A | 11/1992 | Kawaguchi |
| 5,327,901 A | 7/1994 | Delente |
| 5,346,089 A | 9/1994 | Brown |
| 5,432,094 A | 7/1995 | Delente |
| 5,467,776 A | 11/1995 | Hamilton |
| 5,711,306 A | 1/1998 | Guilluy |
| 6,016,122 A * | 2/2000 | Chen ........................... 137/223 |

* cited by examiner

*Primary Examiner*—Matthew O. Savage
(74) *Attorney, Agent, or Firm*—Ryan Kromholz & Manion SC (57) ABSTRACT

An air sampling device for obtaining an air sample from a person's lungs, and a method for using the same. The air sampling device is comprised of generally of a breath intake structure, an expandable bag structure, an adhesive patch, and a removable adhesive patch cover. Optionally an adhesive inlet seal patch also seals either the expandable bag inlet or an outer shell. The outer shell is provided to capture the air sample should the expandable bag structure fail. A person breathes into the breath intake, the device directing a first predetermined volume of breath into the expandable bag structure, and the remainder of breath also into the expandable bag, the remainder of the breath expelling the first predetermined volume of waste air from the expandable bag structure. The breath intake structure and removable adhesive patch cover are removed and the adhesive patch seals the interior surfaces of the expandable bag structure. The expandable bag structure can include preloaded desiccant or chemical indicator, in order to perform a variety of tests.

12 Claims, 12 Drawing Sheets

SEALABLE AIR SAMPLING BAG

BACKGROUND OF THE INVENTION

1. Field of the Invention

This invention relates to the field of sampling air from the lungs and specifically to the field of obtaining a sample of a person's air, including alveolar air from the alveoli of the lungs of a person.

2. Description of the Prior Art

Air from the lungs of a person can be used for many different types of testing that would otherwise require the person to undergo an invasive procedure. For example, alveolar air can be analyzed for, but not limited to, the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, necessary for specific testing.

A simple to use, inexpensive, and user-friendly apparatus is desired to collect and store human breath samples. In order to collect true alveolar air, an apparatus smaller in potential volume than the volume of a human breath is desired, in order to purge air from the apparatus and subject to be tested that is not true alveolar air. One such apparatus is disclosed in U.S. Pat. 5,432,094 to Delente (Jul. 11, 1995). Another such apparatus is disclosed in U.S. Pat. 5,327,901 to Delente (Jul. 12, 1994).

However, the two Delente disclosures are not flexible and depend on rigid storage means. Additionally, the two Delente disclosures begin with storage means that are originally filled with ambient air. Because the Delente disclosures are filled with ambient air, the ambient air must first be purged from the storage means. This allows for the possibility that the sample will ultimately contain a portion of ambient air, as opposed to containing entirely human breath.

Often it is necessary to transport the air sample in the sample container for long distances, frequently by airplanes to the location of a special gas analyzer. It is necessary to have a sample container that is cost efficient, light weight, dependable and capable of withstanding contraction and expansion common to high elevation and pressure changes without bursting and losing the sample. Additionally, it is desirable to have a sample container that is easy to operate, without risk of sample contamination due to dilution, diffusion, or through interaction of the sample and container materials.

SUMMARY OF THE INVENTION

An air sampling device for sampling air received from the exhalation of breath of a person is disclosed. The air sampling device is comprised of a breath intake structure used to exhale a breath into an expandable bag structure through an inlet. The breath intake structure can be constructed of commonly available materials, and a drinking straw may be the preferred breath intake structure. The expandable bag structure is preferably constructed of a supple, airtight, gas impermeable, and inert material.

An adhesive patch is adhered to an interior surface of the inlet, and the adhesive patch is selectively covered by a removable adhesive patch cover selectively adhered the first side of the adhesive patch. The breath intake structure is selectively communicatively coupled with expandable bag structure through the inlet, between a second interior surface of the inlet and the removable adhesive patch cover.

The adhesive patch is coextensive with the inlet at one end, and another end extends into the interior of the expandable bag structure. The removable adhesive patch cover is at one end coextensive with the adhesive patch first end, and the removable adhesive patch cover extends into the expandable bag structure interior at least to the adhesive patch second end, and the other end of the removable adhesive patch cover extends out of the inlet.

An adhesive inlet seal patch is provided to supply additional seal to the expandable bag structure, beyond the seal provided by the adhesive patch. The adhesive inlet seal patch can be labeled with a sample identifier, such as possibly a barcode or machine-readable system. The sample identifier provides a convenient method for sequentially labeling air samples, or should the samples include a preloaded dessicant or a chemical indicator, or should samples from different patients be shipped together.

In another embodiment of the present invention, the air sampling device can include an outer shell encapsulating the expandable bag structure. The outer shell can capture the air sample should the expandable bag structure rupture. The outer shell has an outer shell inlet to the expandable bag structure interior providing a conduit for the breath intake structure. In this embodiment, the breath intake structure is selectively communicatively coupled with the expandable bag structure interior between the one interior surface of the expandable bag structure inlet and the removable adhesive patch cover. In this embodiment, the adhesive inlet seal patch is applied to the exterior of the outer shell. Again, the adhesive inlet seal patch can include the sample identifier. The outer shell is sized to contain a volume greater than a volume of the inner expandable bag structure, so that if the air sample is depressurized and ruptures the inner expandable bag structure, the outer shell will still contain the air sample.

A method for using the air sampling device is also disclosed and is substantially as follows. The breath intake structure is inserted into the expandable bag structure inlet between a second interior surface of the inlet and the removable adhesive patch cover. A patient places the breath intake structure into the mouth against his or her lips and exhales into it in a normal manner. During an initial phase of a patient's exhalation into the breath intake structure, the expired air flows into the initially empty expandable bag structure, filling the expandable bag structure. During the remaining phase of the patient's exhalation through the intake structure, the breath from the initial phase of the patient's exhalation is expelled through the inlet, and is replaced by alveolar air that remains in the expandable bag structure.

To seal the expandable bag structure, the breath intake structure and removable adhesive patch cover are grasped and withdrawn from the expandable bag structure interior and the exterior surfaces of the inlet are pressed together, adhering the interior surfaces against the adhesive patch.

Next, to further seal the expandable bag structure if desired, the adhesive inlet seal patch is separated from the adhesive inlet seal patch cover, and the adhesive inlet seal patch is applied to the expandable bag structure, further sealing the inlet. The sample identifier can be either written or pre-labeled on the adhesive inlet seal patch or outer shell.

If an outer shell is employed, the same sampling methodology is used, with the exception that following the step of pressing together the exterior surfaces of the inlet with the adhesive patch, the adhesive inlet seal patch is separated from the adhesive inlet seal patch cover, and the adhesive inlet seal patch is applied to the outer shell, covering the outer shell inlet.

If the expandable bag structure bursts, the outer shell will still contain the air sample. Accordingly, when a person exhales into the breath intake structure, a first predetermined volume of breath enters the expandable bag structure until the expandable bag structure is expanded to its predetermined size Next, the remainder of the breath, which includes alveolar air from the person's lungs, enters and expands the expandable bag structure and forces the waste air from the expandable bag structure. This results in the expandable bag being filled with a sample of alveolar air.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to FIGS. 1A–H, FIGS. 2A–D, and FIGS. 3A and B, an air sampling device for sampling air received from the exhalation of breath of a person is disclosed. The air sampling device is comprised of a breath intake structure 22 used to exhale a breath 22 into an expandable bag structure 30 having an interior 32, and an inlet 36 in the expandable bag structure 30 to the expandable bag structure interior 32. The inlet 36 has a first interior surface 38, a second interior surface 40, a first exterior surface 42, and a second exterior surface 44.

The breath intake structure 22 can be constructed of commonly available materials, and a drinking straw is the preferred breath intake structure. However, the breath intake structure 22 could vary widely to include mouthpieces of varying structure. The expandable bag structure 30 is preferably constructed of a supple, inert, and airtight material. One such supple and airtight material that performs suitable is thin polyester film, but foil laminate and a variety of other materials could also perform suitably. It should be easily recognizable to one skilled in the art that any number of materials other than foil laminate can be used for the expandable bag structure 30. Other examples of materials that could be used for constructing the present invention include for illustration, but not by way of limitation, include Tedlar®, Saranex®, Saran®, and Teflon®. Those skilled in the art will appreciate that the material can vary widely based on the characteristics of the gases desired to be sampled. The materials chosen should be inert and exhibit relative impermeability to the gases desired to sample, and any materials chosen that are relatively permeable to the gases desired to sample would not be preferred.

An adhesive patch 50 having a first side 52 and a second side 54, and having adhesive on both sides, is adhered to the first interior surface 38 of the inlet 36, and the adhesive patch 50 is selectively covered by a removable adhesive patch cover 60 selectively adhered the first side of the adhesive patch 52.

The breath intake structure 20 is selectively communicatively coupled with expandable bag structure interior 32 through the inlet 36, between the second interior surface 40 of the inlet 36 and the removable adhesive patch cover 60.

Figure 1A:
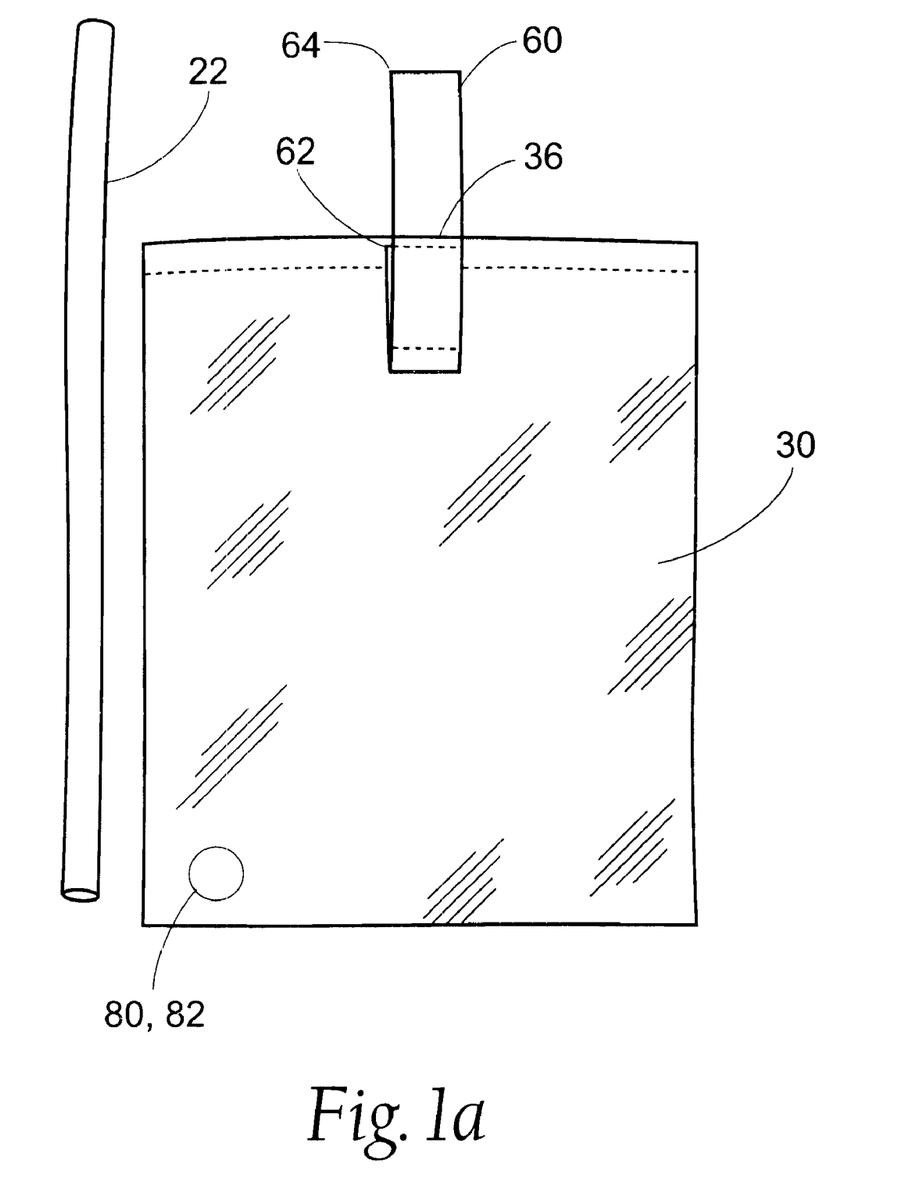
FIG. 1A is a perspective view of one embodiment of an air sampling device.
Figure 1B:
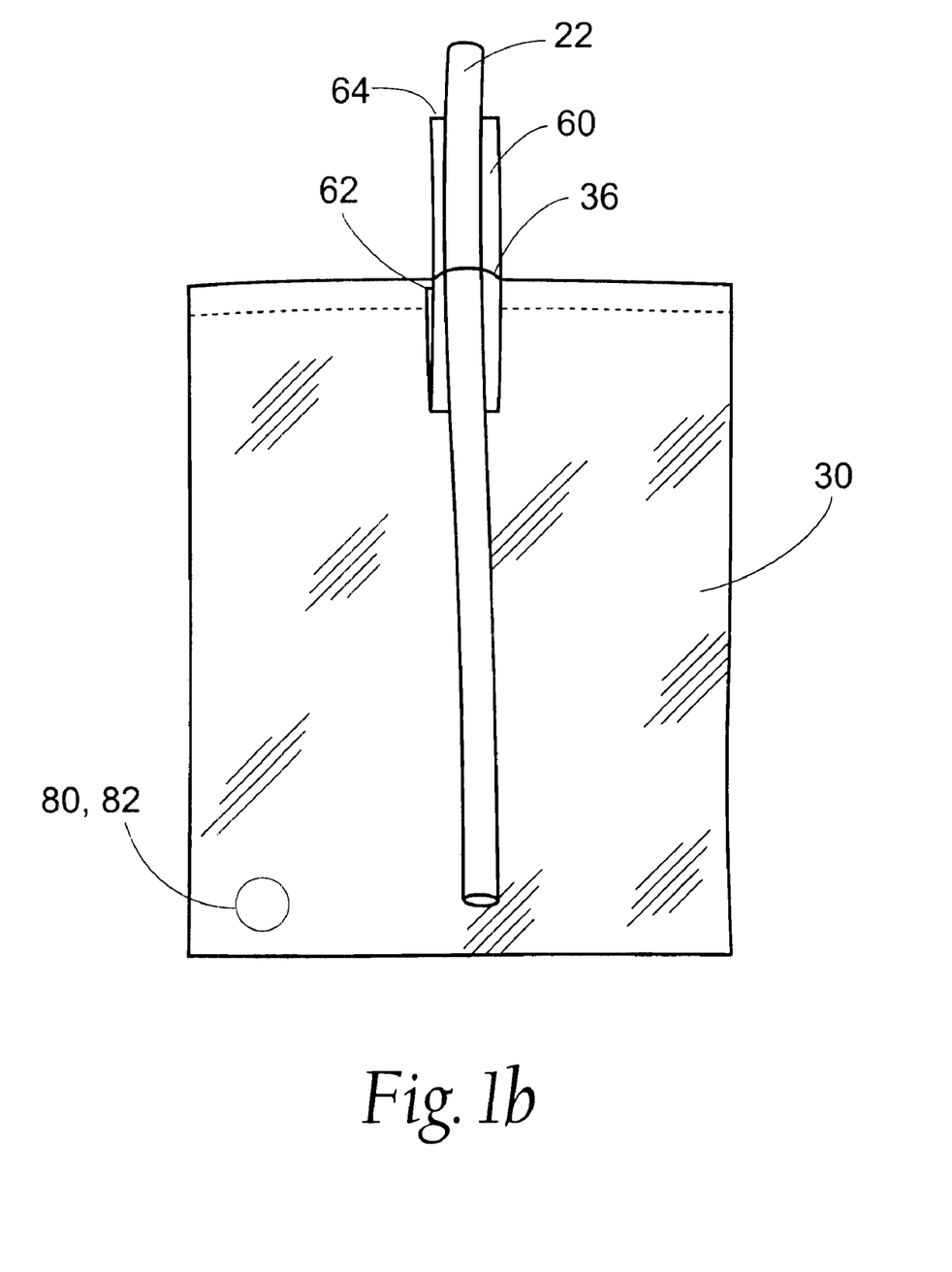
FIG. 1B is a perspective view of an air sampling device with a breath intake structure inserted into the interior of an expandable bag structure.
Figure 1C:
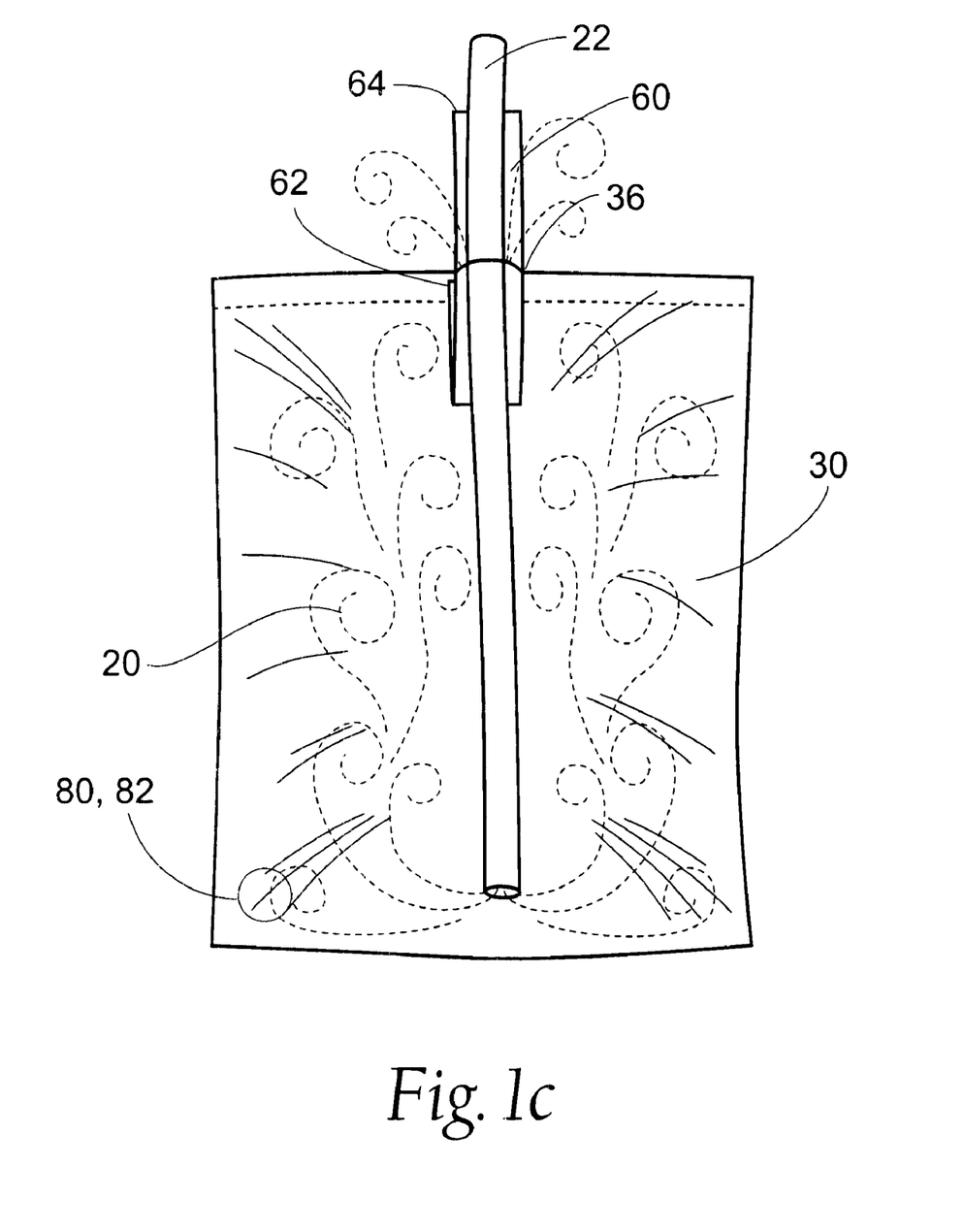
FIG. 1C is a perspective view of an air sampling device with a breath intake structure inserted into the interior of an expandable bag structure, and breath entering the expandable bag structure, with waste air leaving the expandable bag structure.
Figure 1D:
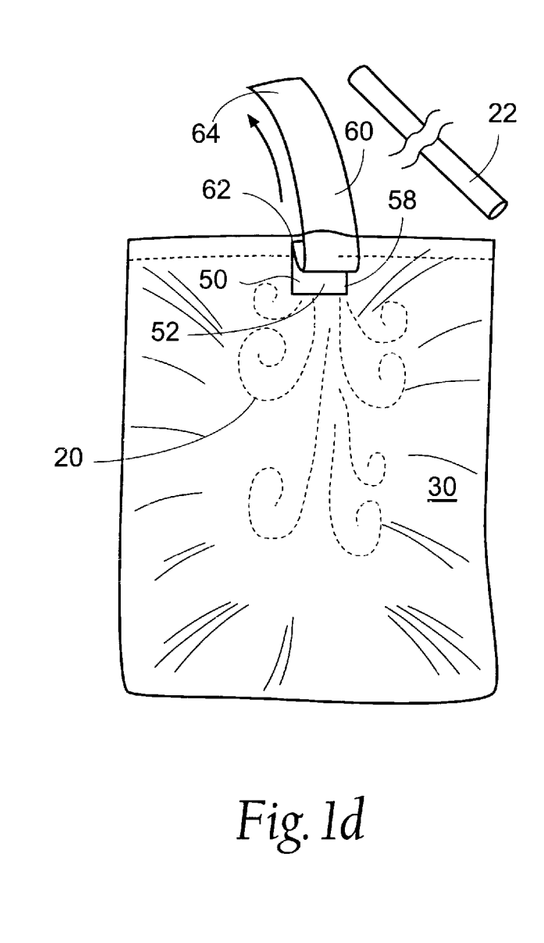
FIG. 1D is a perspective view of an air sampling device with the breath intake structure withdrawn during closure of the expandable bag structure.
Figure 1E:
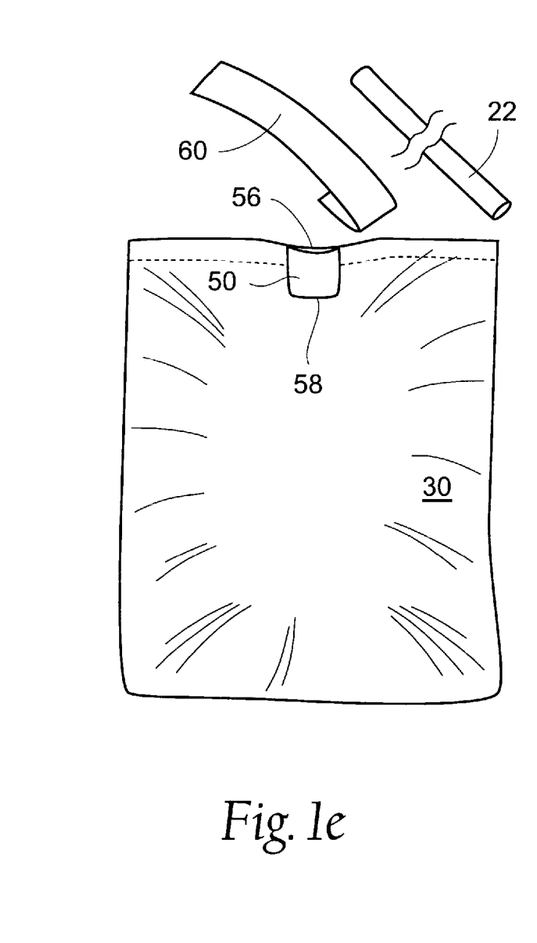
FIG. 1E is a perspective view of an air sampling device following closure.
Figure 2A:
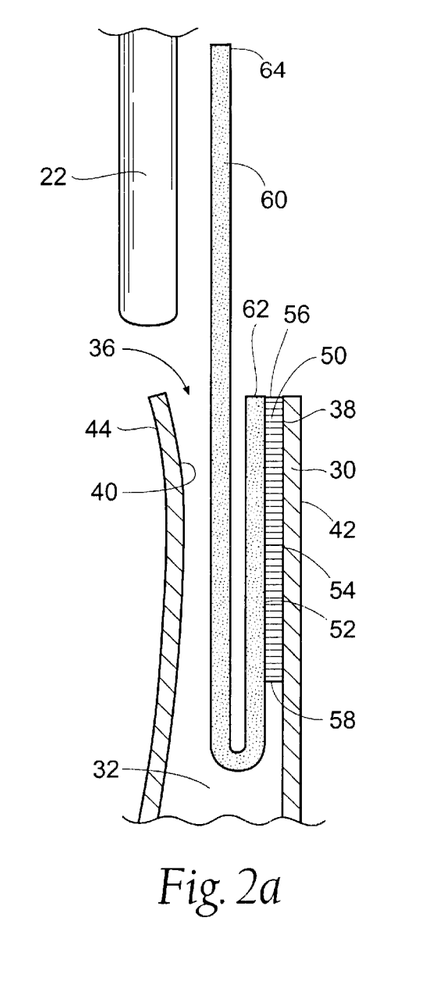
FIG. 2A is a cross sectional view of an inlet to a closed air sampling device, and a breath intake structure, removable adhesive patch cover, and adhesive patch.

In a preferred embodiment, as shown on FIGS. 1E and 2A, the adhesive patch 50 is applied to the first interior surface 38 of the inlet 36, and has two ends; a first end 56 coextensive with the inlet 36, and a second end 58 extending into the interior of the expandable bag structure.

The removable adhesive patch cover 60 has two ends; a first end 62 coextensive with the adhesive patch first end 56, the removable adhesive patch cover 60 extending into the expandable bag structure interior 32 at least to the adhesive patch second end 58, and a second end 64 of the removable adhesive patch cover 60 extending out of the inlet 36.

An adhesive inlet seal patch 70 having a first side 72 and a second side 74 is supplied to supply additional seal to the expandable bag structure, beyond the seal provided by the adhesive patch 50. The adhesive inlet seal patch 70 has adhesive on the first side 72, and an adhesive inlet seal patch cover 76 selectively adhered to the first side 72. The first side 72 of the adhesive inlet seal patch 70 is selectively adherent to the first exterior surface 42 of the expandable bag structure inlet 36 and the second exterior surface 44 of the expandable bag structure inlet 36, when the adhesive inlet seal patch cover 76 is removed from the adhesive inlet seal patch 70. Also preferred, the adhesive inlet seal patch 70 is larger than the expandable bag structure inlet 36, such that air could not escape the expandable bag structure inlet 36 when the adhesive inlet seal patch 70 is properly applied.

In a preferred embodiment, the second side 74 of the adhesive inlet seal patch 70 is labeled with a sample identifier 78. The sample identifier 78 provides a convenient method for labeling air samples, should the samples include a preloaded dessicant 80 or a chemical indicator 82, or should samples from different patients be shipped together. The sample identifier 78 could comprise, for example, a written indicia of identification, or could comprise a barcode or machine readable indicia. Of course, the sample identifier 78 need not be applied to the adhesive inlet seal patch 70; the sample identifier 78 could be applied anywhere on the air sampling device. However, the adhesive inlet seal patch 70 is a preferable location for the sample identifier 78 because this portion of the air sampling device would likely be the most amenable for feeding through bar code application devices or printer devices.

The air sampling device can include at least one of the preloaded desiccant 80 and the chemical indicator 82 within the interior of the expandable bag structure 30. The preloaded desiccant 80 or chemical indicator 82 can be included for a variety of purposes, including for example with alkaline hygroscopic material to dry the sample, or with chemical indicators to perform different tests on the air sample.

Figure 4:
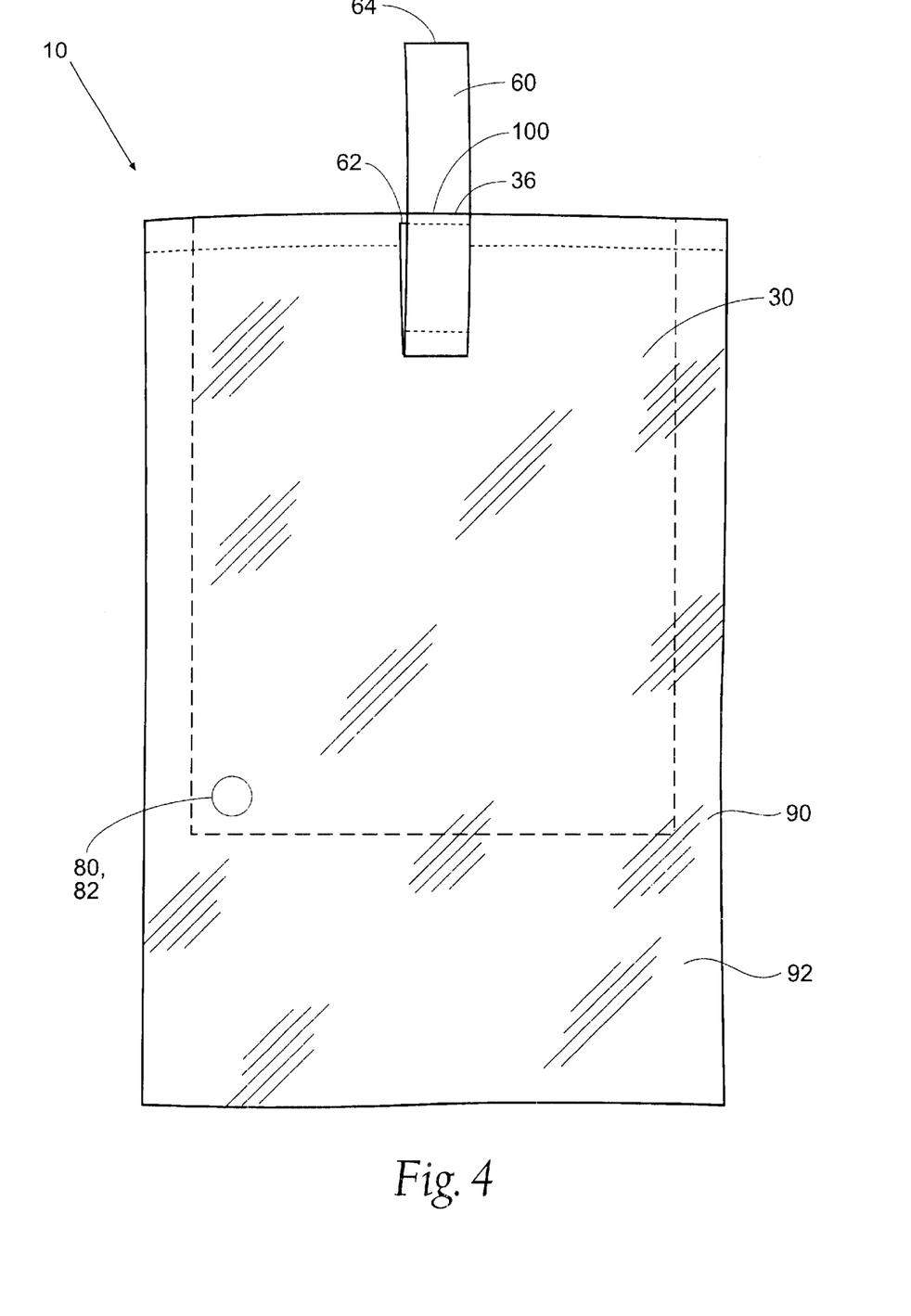
FIG. 4 is a perspective view of another embodiment of an air sampling device, including an outer shell encapsulating an expandable bag structure.

Referring now to FIG. 4, in another embodiment of the present invention, the air sampling device 10 can include an outer shell 90 having an interior 92 encapsulating the expandable bag structure 30. The outer shell 90 can capture the air sample should the expandable bag structure 30 rupture, as is shown in FIG. 5B. The outer shell 90 has an outer shell inlet 100 to the expandable bag structure interior 32, the outer shell inlet 100 creating a void in the outer shell 90.

Preferably, the outer shell inlet 100 is coextensive with the first and second exterior surfaces 42 and 44 of the expandable bag structure inlet 36. In this embodiment, the breath intake structure 22 is selectively communicatively coupled with the expandable bag structure interior 32 through the outer shell inlet 100 and through the expandable bag structure inlet 36, between the expandable bag structure inlet second interior surface 40 and the removable adhesive patch cover 60. In this embodiment, the adhesive inlet seal patch 70 is applied to the exterior of the outer shell 90, as opposed to the expandable bag structure 30. Again, the adhesive inlet seal patch 70 can include the sample identifier 78.

Preferably, the outer shell 90 is made of supple, inert, air-tight material such as laminated metal foil, and therefore the alveolar air sample remains in it for a substantially long period of time. The outer shell 90 is sized to contain a volume greater than a volume of the expandable bag structure 30, so that if the air sample is depressurized and ruptures the expandable bag structure 30, the outer shell will still contain the air sample.

Figure 1F:
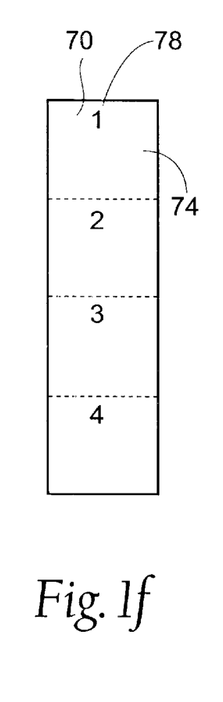
FIG. 1F is a perspective view of an adhesive inlet seal patch and sample identifier.
Figure 1G:
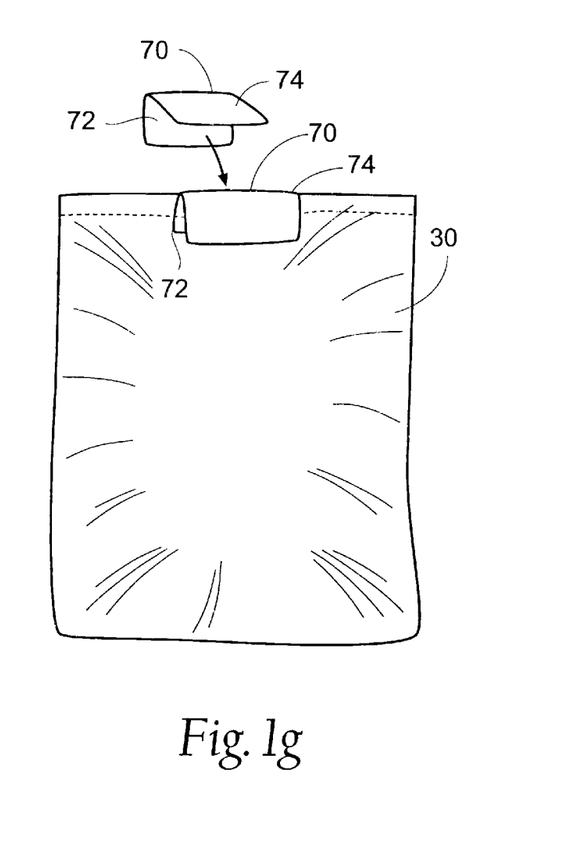
FIG. 1G is a perspective view of an air sampling device following closure during application of the adhesive inlet seal patch and sample identifier.
Figure 1H:
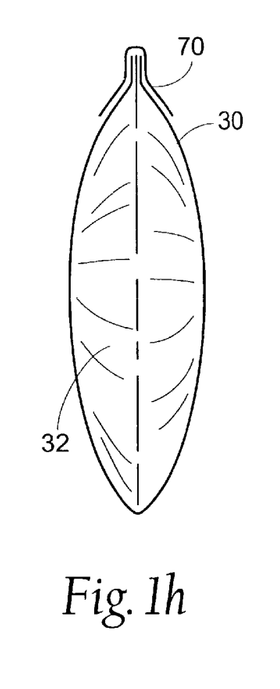
FIG. 1H is a perspective side view of a closed air sampling device containing a breath sample.
Figure 2B:
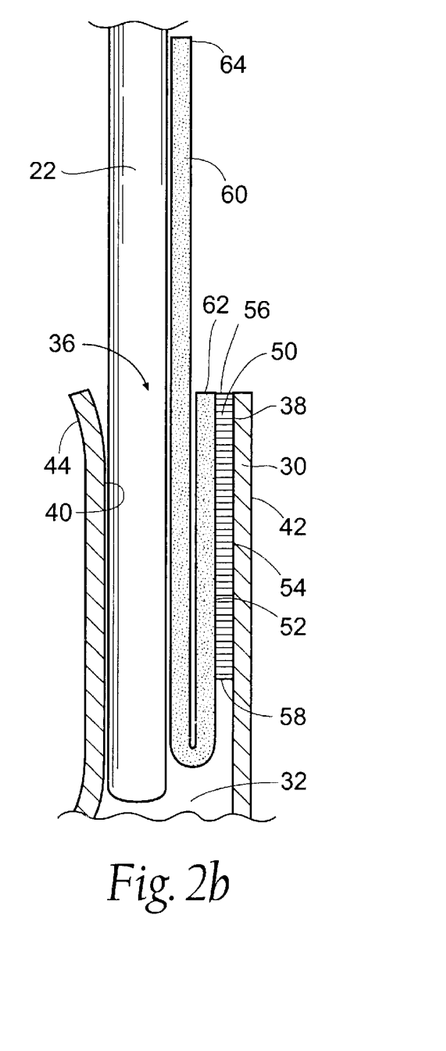
FIG. 2B is a cross sectional view of an inlet to a closed air sampling device, the breath intake structure inserted into the inlet between the removable adhesive patch cover and an interior surface of an expandable bag structure inlet, and an adhesive patch.

Referring to FIGS. 1A–H, FIGS. 2A–D, the air sampling device is used substantially as follows. The breath intake structure 22 is inserted into the expandable bag structure inlet 36 between the expandable bag structure second interior surface 40 and the removable adhesive patch cover 60, as shown in FIGS. 1B and 2B.

To collect a sample of a patient's expired alveolar air, the patient places the breath intake structure 22 against his or her lips and exhales into it in a normal manner. During an initial phase of a patient's exhalation into the breath intake structure 22, the expired air flows into the initially empty expandable bag structure 30, filling the expandable bag structure 30. During the remaining phase of the patient's exhalation, a portion of the breath from the initial phase of the patient's exhalation is expelled through the inlet 36 as shown in FIG. 1C, leaving alveolar air remaining in the expandable bag structure 30. The expandable bag structure 30, which is made from a supple and airtight material, is brought to full inflation by the exhalation of the person. This causes the removal from the lungs and bronchial tree of what is referred to as "dead space air", i.e. the air that issues from the oral cavity, the nose, the trachea, and the bronchi of the person during the initial phase of exhalation of the person. After the undesired air has been expelled from the expandable bag structure 30, the remainder of the breath or a portion of the remainder of the breath including the desired alveolar air located deep within the lungs, is exhaled, filling expandable bag structure 30.

Figure 2C:
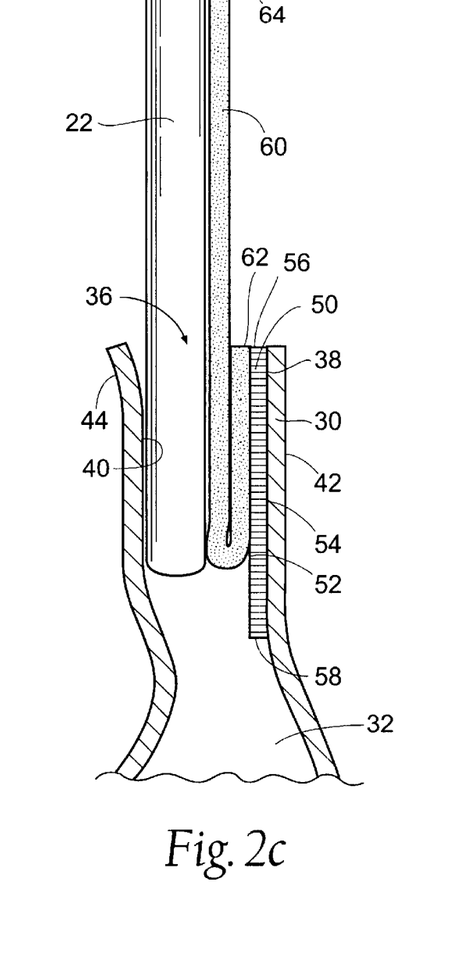
FIG. 2C is a cross sectional view of an inlet to a closed air sampling device, the breath intake structure being withdrawn from the inlet between the removable adhesive patch cover and an interior surface of an expandable bag structure inlet, and an adhesive patch.
Figure 2D:
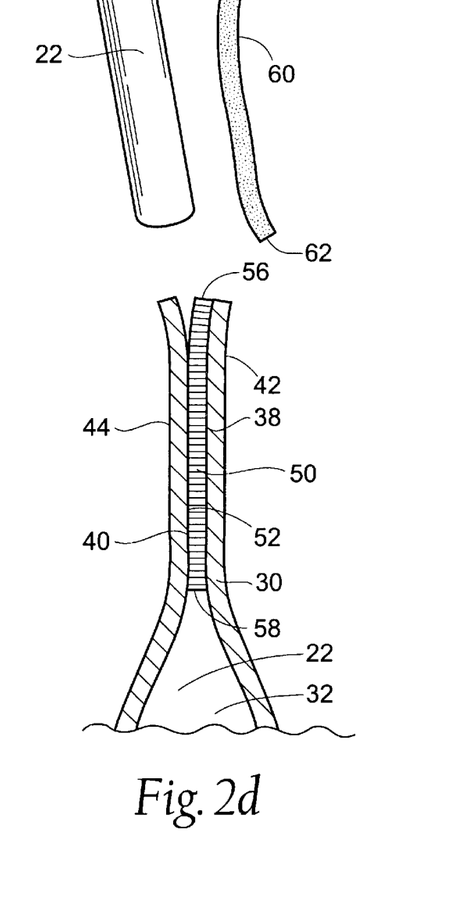
FIG. 2D is a cross sectional view of an inlet to a closed air sampling device, the breath intake structure and the removable adhesive patch cover fully withdrawn from the expandable bag structure inlet, and the adhesive patch adhered to two interior surfaces of the expandable bag structure inlet, sealing the expandable bag structure.

To seal the expandable bag structure 30, the breath intake structure 22 and removable adhesive patch cover second end 64 are grasped and withdrawn from the expandable bag structure interior 32, as shown in FIG. 2C. Next the first and second exterior surfaces 42 and 44 of the inlet 36 are pressed together, adhering the first and second interior surfaces 38 and 40 against the adhesive patch 50 as shown in FIGS. 2D and 1E.

Figure 3A:
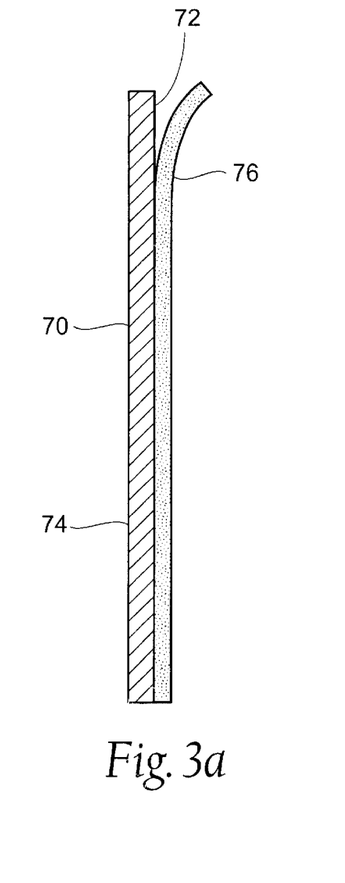
FIG. 3A is a cross sectional view of an adhesive inlet seal patch and adhesive inlet seal patch cover.
Figure 3B:
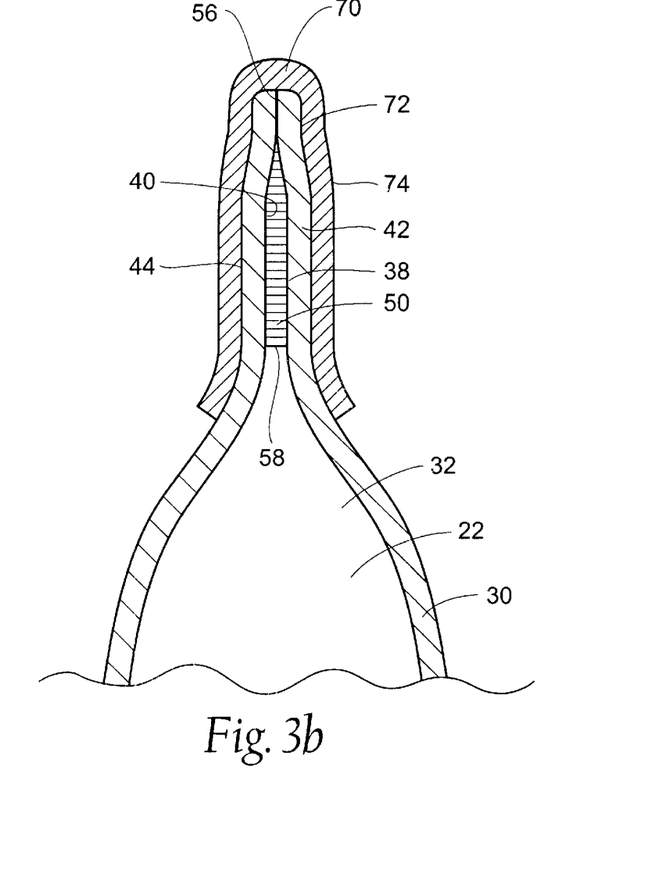
FIG. 3B is a cross sectional view of an inlet to a closed air sampling device, the breath intake structure and the removable adhesive patch cover fully withdrawn from the expandable bag structure inlet, the adhesive patch adhered to two interior surfaces of the expandable bag structure inlet, sealing the expandable bag structure, the adhesive inlet seal patch cover removed from the adhesive inlet seal patch, and the adhesive inlet seal patch applied to two exterior surfaces of the expandable bag structure inlet and the expandable bag structure.

Next, to further seal the expandable bag structure if desired, the adhesive inlet seal patch 70 is separated from the adhesive inlet seal patch cover 76 as shown in FIG. 3A, and the adhesive inlet seal patch 70 is applied to the expandable bag structure 30 at the first and second exterior surfaces 42 and 44 of the inlet 36 as shown in FIGS. 1G and 3B, further sealing the inlet. The sample identifier 78 can be either written or pre-labeled on the adhesive inlet seal patch 70, as shown in FIG. 1F.

If an outer shell 90 is employed, the same sampling methodology is used, with the exception that following the step of pressing together the first and second exterior surfaces 42 and 44 of the inlet 36 with the adhesive patch 50, the adhesive inlet seal patch 70 is separated from the adhesive inlet seal patch cover 76, and the adhesive inlet seal patch 70 is applied to the outer shell 90, covering the outer shell inlet 100.

Figure 5A:
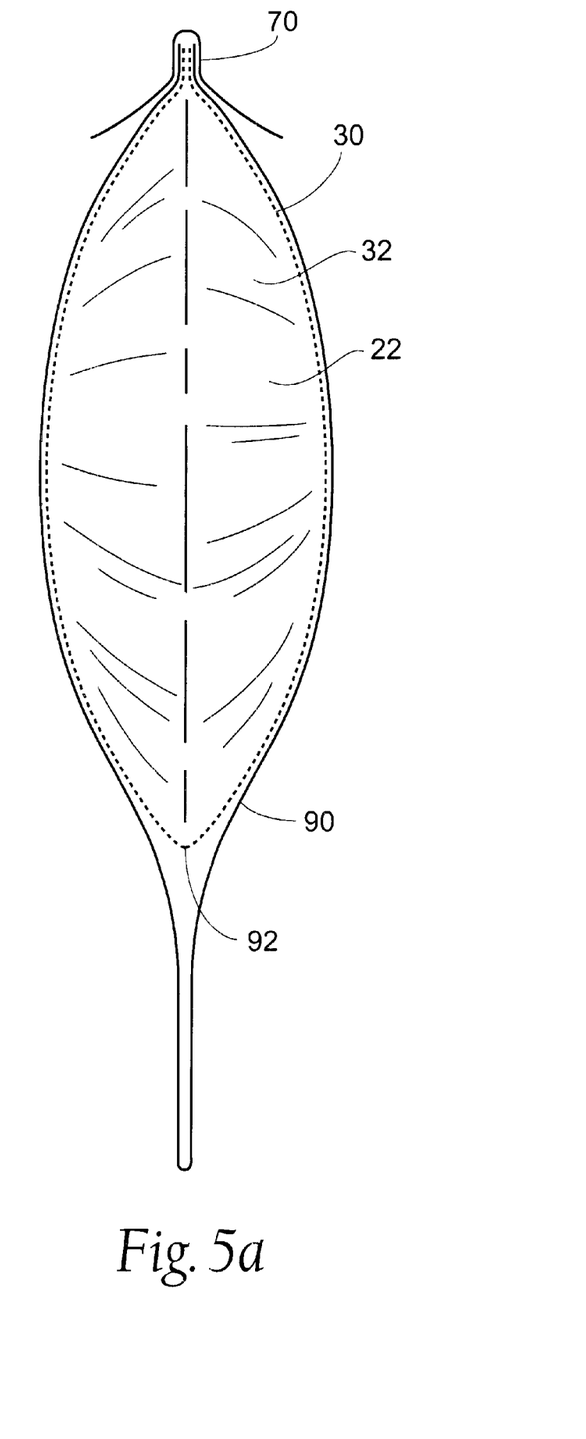
FIG. 5A is a side perspective view of an air sampling device including an outer shell, the expandable bag structure containing a breath sample.
Figure 5B:
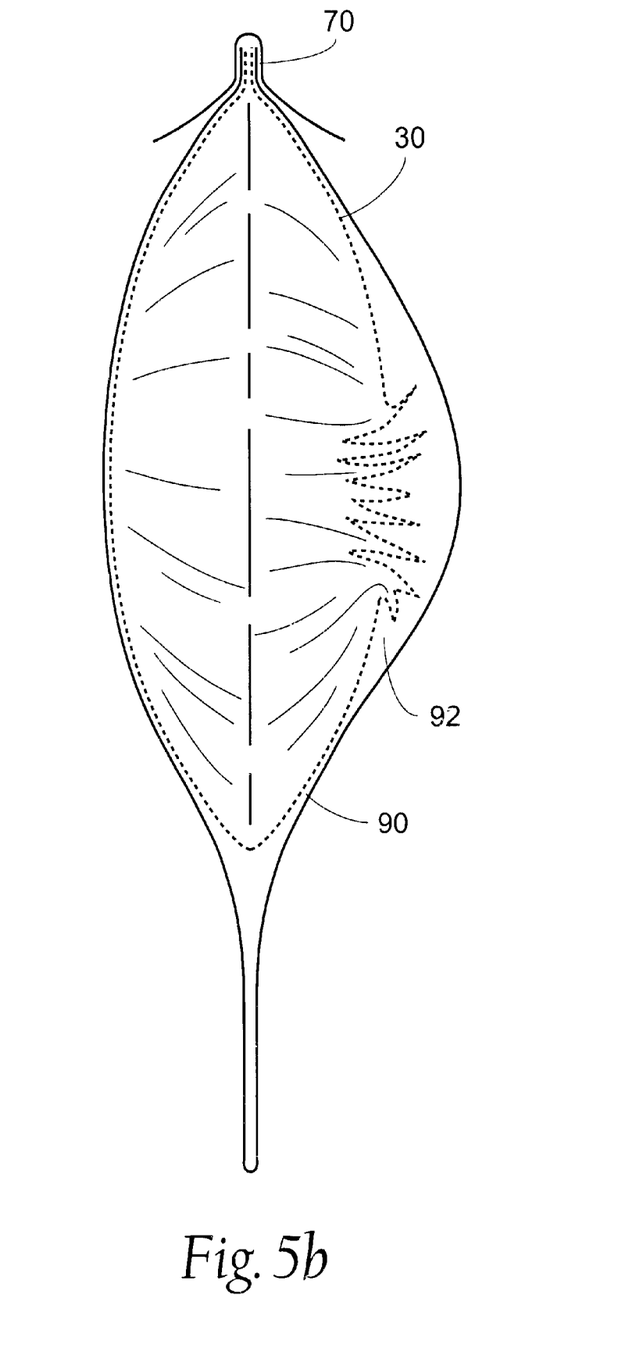
FIG. 5B is a side perspective view of an air sampling device including an outer shell, the expandable bag structure bursting.
Figure 5C:
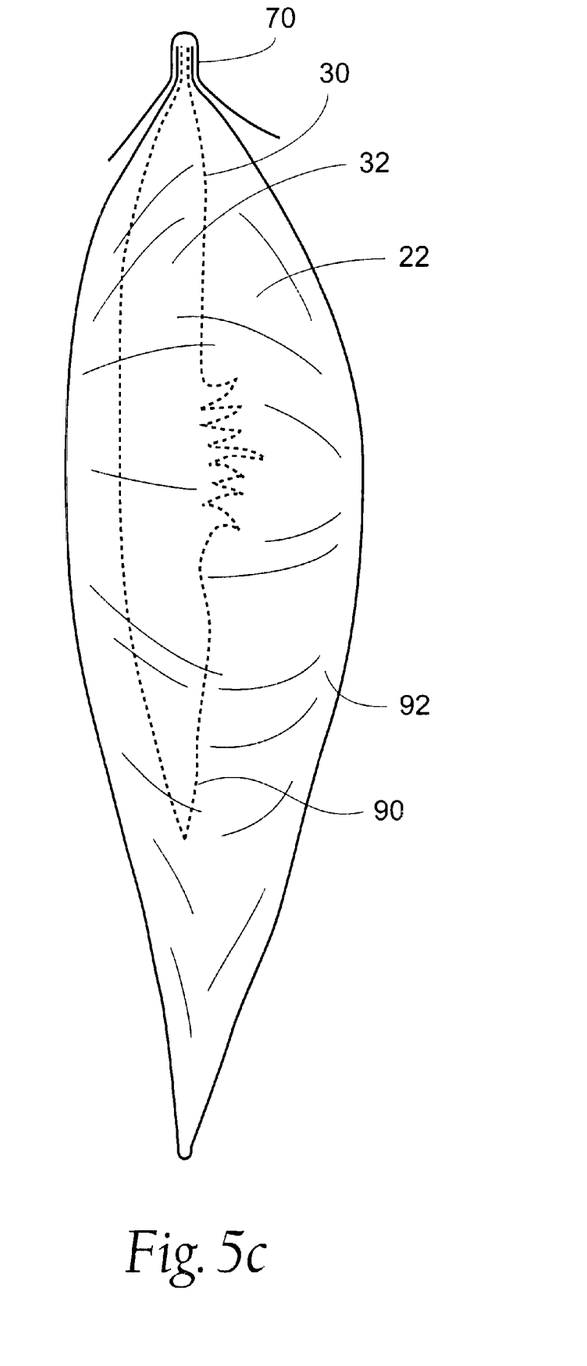
FIG. 5C is a side perspective view of an air sampling device including an outer shell, the expandable bag structure burst, and the outer shell capturing the breath sample.

If the outer shell 90 is used, the expandable bag structure 30 is filled as shown in FIG. 5A. Next, if the expandable bag structure 30 bursts, as shown in FIG. 5B, the outer shell 90 will still contain the air sample, as shown in FIG. 5C. This feature is particularly useful if the samples must be transported by airplane, exposing the samples to wide pressure and temperature variations.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An air sampling device for sampling air received from the exhalation of breath of a person, said air sampling device comprising:

a breath intake structure;

an expandable bag structure having an interior;

an inlet in the expandable bag structure to the expandable bag structure interior, the inlet having at least one of a first interior surface and a second interior surface, and at least one of a first exterior surface and a second exterior surface;

an adhesive patch having a first side and a second side, and having adhesive on both sides, the second side of the adhesive patch adhered to at least one of the first and second interior surfaces of the inlet;

a removable adhesive patch cover selectively adhered the first side of the adhesive patch;

the breath intake structure selectively communicatively coupled with the interior of the expandable bag structure through the inlet, between the second interior surface of the inlet and the removable adhesive patch cover;

an adhesive inlet seal patch having a first side and a second side, the adhesive inlet seal patch having adhesive on the first side of the adhesive inlet seal patch;

an adhesive inlet seal patch cover selectively adhered to the first side of the adhesive seal inlet patch;

the first side of adhesive seal patch selectively adherent to the first and second exterior surfaces of the inlet, when the adhesive inlet seal patch cover is removed from the adhesive inlet seal patch.

2. An air sampling device according to claim 1, wherein the air sampling device is labeled with a sample identifier.

3. An air sampling device according to claim 2, wherein the sample identifier is applied to the second side of the adhesive inlet seal patch.

4. An air sampling device according to claim 2, wherein the sample identifier comprises a bar code.

5. An air sampling device according to claim 1, the air sampling device further comprising at least one of a preloaded desiccant and a chemical indicator contained within the interior of the expandable bag structure.

6. An air sampling device according to claim 1, the air sampling device further comprising:

an outer shell encapsulating the expandable bag structure, the outer shell having an interior;

an outer shell inlet to the expandable bag structure interior, the outer shell inlet creating a void in the outer shell.

7. An air sampling device according to claim 6, wherein the outer shell inlet is coextensive with the first and second exterior surfaces of the expandable bag structure inlet.

8. An air sampling device according to claim 7, wherein the breath intake structure is selectively communicatively coupled with the interior of the expandable bag structure through the outer shell inlet and through the expandable bag structure inlet, between the second interior surface of the expandable bag structure inlet and the removable adhesive patch cover.

9. An air sampling device for sampling air received from the exhalation of breath of a person, said air sampling device comprising:

a breath intake structure;

an expandable bag structure having an interior;

an inlet in the expandable bag structure to the expandable bag structure interior, the inlet having at least one of a first interior surface and a second interior surface, and at least one of a first exterior surface and a second exterior surface;

an adhesive path having a first side and a second side, and having adhesive on both sides, the second side of the adhesive path adhered to at least one of the first and second interior surfaces of the inlet;

a removable adhesive patch cover selectively adhered the first side of the adhesive patch;

the breath intake structure selectively communicatively coupled with the interior of the expandable bag structure through the inlet, between the second interior surface of the inlet and the removable adhesive patch cover;

an outer shell encapsulating the expandable bag structure, the outer shell having an interior an outer shell inlet to the expandable bag structure interior, the outer shell inlet creating a void in the outer shell wherein the outer shell inlet is coextensive with the first and second exterior surfaces of the expandable bag structure inlet wherein the breath intake structure is selectively communicatively coupled with the interior of the expandable bag structure through the outer shell inlet and through the expandable bag structure inlet, between the second interior surface of the expandable bag structure inlet and the removable adhesive patch cover.

10. An air sampling device according to claim 9, wherein the second side of the adhesive inlet seal patch is labeled with a sample identifier.

11. An air sampling device according to claim 9, wherein the outer shell is constructed of foil laminate.

12. An air sampling device according to claim 9, wherein the outer shell is capable of containing a volume greater than a volume of the expandable bag structure when expanded.

* * * * *